United States Patent [19]

Anzeveno

[11] Patent Number: 4,908,439
[45] Date of Patent: Mar. 13, 1990

[54] SYNTHESIS OF INTERMEDIATE USEFUL IN THE PREPARATION OF NOJIRIMYCIN AND RELATED COMPOUNDS

[75] Inventor: Peter Anzeveno, Zionsville, Ind.

[73] Assignee: Merrell Dow Pharmaceuticals Inc., Cincinnati, Ohio

[21] Appl. No.: 245,848

[22] Filed: Sep. 16, 1988

[51] Int. Cl.$^4$ .............................................. C07H 17/02
[52] U.S. Cl. .................................. 536/17.4; 536/17.9; 252/188.26; 252/188.27
[58] Field of Search .................. 536/17.4; 252/188.26, 252/188.27

[56] References Cited

U.S. PATENT DOCUMENTS 4,634,765  1/1987  Liu ..................................... 536/17.4

FOREIGN PATENT DOCUMENTS 3628486  2/1988  Fed. Rep. of Germany .

OTHER PUBLICATIONS

B. P. Bashyal et al., *Tetrahedron Letters*, 27(27), 3205–3208 (1986).
B. P. Bashyal et al., *Tetrahedron*, 43(2), 415–422 (1987).
Y. Tsuda et al., *Heterocycles*, 27(1), 63–66 (1988).
Hudlicky, Milos, *Reductions in Organic Chemistry*, Halsted Press: New York, 1984, pp. 76, 152–154.

*Primary Examiner*—Joseph L. Schofer
*Assistant Examiner*—Gary L. Kunz
*Attorney, Agent, or Firm*—John J. Kolano

[57] ABSTRACT

5-Amino-5-deoxy-1,2-O-isopropylidene-α-D-glucofuranose is conveniently prepared by a hydride reduction of 5-azido-5-deoxy-1,2,O-isopropylidene-α-D-glucuronolactone and can readily be converted to nojirimycin, deoxynojirimycin or homonojirimycin.

4 Claims, No Drawings

SYNTHESIS OF INTERMEDIATE USEFUL IN THE PREPARATION OF NOJIRIMYCIN AND RELATED COMPOUNDS

BACKGROUND OF THE INVENTION

Homonojirimycin glycosides have been described in U.S. Pat. No. 4,634,765 as inhibitors of carbohydrate digestive enzymes and as antidiabetic compounds. The indicated compounds are prepared by the reaction of a protected glycosyl halide with an appropriately protected homonojirimycin compound. In the process described in the patent, the protected homonojirimycin compound is obtained by a cumbersome multi-step synthesis starting with the tetrabenzyl ether of D-glucopyranose. Thus, while the products in the patent would be available by the procedure described there, a method that would avoid the cumbersome synthesis would be attractive. Homonojirimycin itself was not used as an intermediate in the preparation of the protected homonojirimycin compound in U.S. Pat. No. 4,634,765 but it could be used in the overall synthesis if there was a procedure which would give the compound conveniently from available and inexpensive starting materials. Actually, such a procedure would have further value if it could also be used for the preparation of nojirimycin (a known glucosidase inhibitor) and desoxynojirimycin, with these indicated additional compounds obtained either specifically as intermediates or by appropriate modification of the procedure at some point. However, such a convenient procedure has not been available.

One attractive and available starting material for the synthesis of compounds of the type discussed above would be D-glucuronolactone and reports have appeared in the literature on the use of this material in stereospecific syntheses of polyhydroxylated cyclic amino acids and also the conversion of such an amino acid to desoxynojirimycin. Specifically, Bashyal et al., *Tetrahedron*, 43, 415 (1987) describes procedures whereby D-glucuronolactone is reacted with acetone to give the acetonide and then the free C-5 OH is converted to the corresponding azide. By proper choice of reactions, it is possible to obtain either of the stereoisomeric azides. Bashyal then describes the catalytic reduction of the azide to the corresponding amine with the reaction mixture being treating immediately with benzyl chloroformate so that the amine product of the reduction is actually isolated as the corresponding carbamate. The acetonide group is then cleaved with acid to give the corresponding dihydroxy compound which is then hydrogenated in acetic acid to give, by a series of reactions, a trihydroxypipecolic acid. Bashyal also describes the hydrolysis of the azido acetonide to remove the acetonide and give the corresponding dihydroxy compound, followed by catalytic hydrogenation in acetic acid to also give a trihydroxypipecolic acid.

Bayer German OLS 36 28 486 also includes a similar conversion of an azido acetonide to a trihydroxypipecolic acid and, while the Bayer procedure appears to consist of more individual reaction steps, there was no effort to isolate any compound until the final pipecolic acid was obtained. It is noted that Bayer also includes a description of the reduction of this acid with sodium borohydride and boron trifluoride to give desoxynojirimycin.

The synthesis of nojirimycin itself by an entirely different procedure using 5-amino-5-deoxy-1,2-O-isopropylidene-α-D-glucofuranose as an intermediate has been reported by Tsuda et al., *Heterocycles*, 27, 63 (1988). In that procedure, commercially available 1,2-isopropylidene-D-glucofuranose was used as the starting material. The regioselective oxidation of the C5-hydroxyl group in that compound gives the corresponding ketone which is then converted to the O-methyloxime. Reduction of the oxime then gives the amine referred to above. That amine is converted to nojirimycin via the bisulfite adduct by procedures which were previously reported. Although Tsuda indicates that his procedure would be a practical route to nojirimycin without chromatographical separation of the stereoisomers at any stage, nevertheless, it appears that chromatography is used to remove impurities and the conversion of the amine to nojirimycin actually gives a mixture of isomers and it is only because of the favorable crystallization of the nojirimycin bisulfite adduct that it is possible to obtain that material. In addition, although the second isomer remains in solution and does not affect the isolation of the nojirimycin adduct, the fact that it is formed in substantial amounts results in a reduction in the amount of nojirimycin that can be obtained.

SUMMARY OF THE INVENTION

The present invention thus relates to a new process for the synthesis of nojirimycin, homonojirimycin and related compounds and, in particular, to a new conversion which can be used in this synthesis. Specifically, the present invention relates to a new process for the preparation of 5-amino-5-deoxy-1,2-O-isopropylidene-α-D-glucofuranose by a hydride reduction of 5-azido-5-deoxy-1,2-O-isopropylidene-α-D-glucuronolactone. This process can be illustrated structurally as follows:

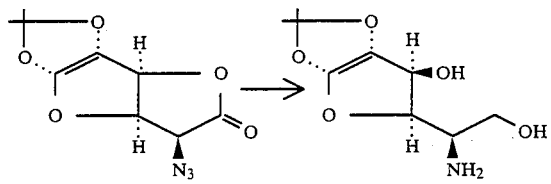

The process is carried out using a hydride reducing agent in an inert solvent. Examples of hydride reducing agents that can be used in the process are lithium aluminum hydride, lithium tri-t-butoxyaluminum hydride, diisobutylaluminum hydride, lithium borohydride and sodium borohydride. Lithium aluminum hydride is the preferred reducing agent for the process. Ethers are the preferred solvent for the reaction with tetrahydrofuran being particularly preferred. The reaction is generally carried out at room temperature without any heating although, once all of the reactants have been mixed, gentle heating and then, ultimately, reflux heating may be used to ensure completion of the reaction.

The process as set forth above is particularly special in that it provides for the simultaneous reduction of the azide group to the amine (with retention of stereochemical configuration) and also reduction of the acid portion of the lactone to the corresponding alcohol. At the same time, the process does not affect the cyclic glucoside portion because it is protected as the isopropylidene ketal. When the ketal protecting group in the resulting product is removed, the glucoside portion of the molecule can open up and then recyclize with the nitrogen and nojirimycin can be obtained.

The 5-azido-5-deoxy-1,2-O-isopropylidene-α-D-glucuronolactone which serves as the starting material in the above process is prepared in five steps from α-D-glucuronolactone by the procedure described by Bashyal et al., *Tetrahedron*, 43, 415 (1987). The 5-amino-5-deoxy-1,2-O-isopropylidene-α-D-glucofuranose obtained as the product of the above process can be converted to nojirimycin bisulfite adduct by the procedure described by Tsuda et al., *Heterocycles*, 27, 63 (1988). The bisulfite adduct can be quantitatively converted to nojirimycin as described by Inouye et al., *Tetrahedron*, 24, 2125 (1968), and nojirimycin can be converted in 97% yield to deoxynojirimycin by the procedure described by Vasella et al., *Helv. Chim. Acta*, 65, 1134 (1982). A conversion of 5-amino-5-deoxy-1,2-O-isopropylidene-α-D-glucofuranose to nojirimycin and then to deoxynojirimycin, by a procedure that does not use the bisulfite adduct of nojirimycin, has been described by Saeki et al., *Chem. Pharm. Bull.*, 16, 2477 (1968). In this case, Saeki et al. obtained the 5-amino-5-deoxy-1,2-O-isopropylidene-α-D-glucofuranose by a different route.

DETAILED DESCRIPTION OF THE INVENTION

A solution of 1.0 g of 5-azido-5-deoxy-1,2-O-isopropylidene-α-D-glucuronolactone in 10 ml of anhydrous tetrahydrofuran was added dropwise, at ambient temperature over a period of 15 minutes, to a well-stirred, nitrogen blanketed suspension of 0.8 g of lithium aluminum hydride in 10 ml of tetrahydrofuran. The mixture warmed to about 40° C. during the addition and hydrogen was evolved. At the end of the addition, the mixture was heated to gentle reflux and refluxed for 18 hours. The mixture was then cooled to 0°–5° C. and quenched by the careful sequential addition of 1.0 ml of water, 2.5 ml of 1N aqueous sodium hydroxide, and 1.0 ml of water. The resulting thick slurry was stirred for 10–15 minutes and finally filtered through Celite. The collected solid was washed with 50 ml of tetrahydrofuran and the combined filtrate and was evaporated to dryness at reduced pressure. The resulting residue was dissolved in 30 ml of acetonitrile and this solution was concentrated to dryness. This material was flash chromatographed over 40 ml of silica using 1:1 methylene chloride-methanol as eluent to give (75% yield) pure 5-amino-5-deoxy-1,2-O-isopropylidene-α-D-glucofuranose. This compound melts at about 120°–121° C. after recrystallization from a mixture of ethanol and ether. $[\alpha]_D^{25} = -16.2°$. $^1$H NMR (300 MHz, d$_6$-DMSO) δ 1.24 (s, 3), 1.39 (s, 3), 3.18 (m, 1), 3.64 (dd, 1, J=11, 4 Hz), 3.95 (dd, 1, J=9, 3 Hz), 4.11 (d, 1, J=3 Hz), 4.43 (d, 1, J=3 Hz), 5.85 (d, J=4 Hz); $^{13}$C NMR (d$_6$-DMSO) δ 26.0, 26.8, 51.5, 61.8, 73.8, 78.8, 85.0, 104.8, 110.8; m/z (CI, CH$_4$) 220 (100), 202 (13), 162 (41), 144 (21), 99 (16).

Nojirimycin bisulfite adduct was prepared from 5-amino-5-deoxy-1,2-O-isopropylidene-α-D-glucofuranose in 55% yield by the procedure of Tsuda et al. [*Heterocycles*, 27, 63 (1988)] and was identical to that from natural nojirimycin in every respect. This bisulfite adduct can be quantitatively interconverted to nojirimycin [Inouye et al., *Tetrahedron*, 24, 2125 (1968)] and the nojirimycin can be converted in 97% yield to deoxynojirimycin [Vasella et al., *Helv. Chim. Acta*, 65, 1134 (1982)]. In addition, nojirimycin can be converted to homonojirimycin by the procedure described by Anzeveno et al. in U.S. Pat. No. 4,880,917.

What is claimed is:

1. A process for preparing 5-amino-5-deoxy-1,2-O-isopropylidene-α-D-glucofuranose which comprises reducing 5-azido-azido-5-deoxy-1,2-O-isopropylidene-α-D-glucuronolactone with a hydride reducing agent selected from the group consisting of lithium aluminum hydride, lithium tri-t-butoxyaluminum hydride, and isobutylaluminum hydride.

2. A process according to claim 1 for preparing 5-amino-5-deoxy-1,2-O-isopropylidene-α-D-glucofuranose which comprises reducing 5-azido-5-deoxy-1,2-O-isopropylidene-α-D-glucuronolactone with lithium aluminum hydride.

3. A process for preparing nojirimycin which comprises reducing 5-azido-5-deoxy-1,2-O-isopropylidene-α-D-glucuronolactone with a hydride reducing, selected from the group consisting of lithium aluminum hydride, tri-t-butoxyaluminum hydride, and isobutylaluminum hydride, to give 5-amino-5-deoxy-1,2-O-isopropylidene-α-D-glucofuranose followed by reaction of the amino compound with aqueous sulfur dioxide to give nojirimycin bisulfite which is then converted to nojirimycin.

4. A process according to claim 3 in which the hydride reducing agent is lithium aluminum hydride.

* * * * *

UNITED STATES PATENT AND TRADEMARK OFFICE
CERTIFICATE OF CORRECTION

PATENT NO. : 4,908,439
DATED : March 13, 1990
INVENTOR(S) : Peter B. Anzeveno

It is certified that error appears in the above-identified patent and that said Letters Patent is hereby corrected as shown below:

Column 2, Line 40 patent reads:

and should read:

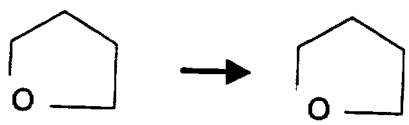

Column 4, Line 26 patent reads: "5-azido-azido-5" and should read: --5-azido-5--.

Column 4, Line 38 patent reads: "reducing, selected" and should read: --reducing agent, selected--.

Signed and Sealed this

Thirtieth Day of July, 1991

Attest:

HARRY F. MANBECK, JR.

Attesting Officer

Commissioner of Patents and Trademarks